(12) United States Patent
Stilwell et al.

(10) Patent No.: US 9,354,172 B2
(45) Date of Patent: May 31, 2016

(54) TUBE AND REFLECTIVE FLOAT SYSTEMS FOR ANALYZING SUSPENSIONS

(75) Inventors: Jackie Lynn Stilwell, Sammamish, WA (US); Arturo Bernardo Ramirez, Seattle, WA (US)

(73) Assignee: RARECYTE, INC., Seattle, WA (US)

( * ) Notice: Subject to any disclaimer, the term of this patent is extended or adjusted under 35 U.S.C. 154(b) by 870 days.

(21) Appl. No.: 13/437,616

(22) Filed: Apr. 2, 2012

(65) Prior Publication Data
US 2013/0153784 A1 Jun. 20, 2013

Related U.S. Application Data

(60) Provisional application No. 61/577,866, filed on Dec. 20, 2011.

(51) Int. Cl.
| | |
|---|---|
| *B01L 3/00* | (2006.01) |
| *G01N 21/64* | (2006.01) |
| *G01N 21/03* | (2006.01) |
| *B01L 99/00* | (2010.01) |

(52) U.S. Cl.
CPC ........ *G01N 21/6428* (2013.01); *B01L 3/50215* (2013.01); *G01N 21/03* (2013.01); *B01L 2300/0636* (2013.01); *B01L 2300/168* (2013.01); *G01N 21/645* (2013.01); *G01N 2021/6439* (2013.01)

(58) Field of Classification Search
USPC ........................................................ 422/500
See application file for complete search history.

(56) References Cited

U.S. PATENT DOCUMENTS

| | | | | |
|---|---|---|---|---|
| 4,630,486 | A | * | 12/1986 | Miles et al. ................. 73/861.56 |
| 5,408,874 | A | * | 4/1995 | Fleck, Sr. ............ G01F 23/2962 367/908 |
| 5,496,704 | A | | 3/1996 | Fiedler et al. |
| 5,560,830 | A | * | 10/1996 | Coleman ............. B01L 3/50215 210/121 |
| 5,736,033 | A | * | 4/1998 | Coleman ................ B01D 21/24 210/122 |
| 6,197,523 | B1 | | 3/2001 | Rimm et al. |
| 6,444,436 | B1 | | 9/2002 | Rimm et al. |
| 6,670,197 | B2 | | 12/2003 | Rimm et al. |
| 6,911,315 | B2 | | 6/2005 | Rimm et al. |
| 7,074,577 | B2 | | 7/2006 | Haubert et al. |
| 7,129,056 | B2 | | 10/2006 | Rimm et al. |
| 7,220,593 | B2 | | 5/2007 | Haubert et al. |
| 7,329,534 | B2 | | 2/2008 | Haubert et al. |
| 7,358,095 | B2 | | 4/2008 | Haubert et al. |
| 7,495,827 | B2 | | 2/2009 | Grimes et al. |
| 7,560,277 | B2 | | 7/2009 | Weller, III |

(Continued)

OTHER PUBLICATIONS

Ramirez, A. et al., "The RareCyte system for enumeration of circulating tumor cells that retains all nucleated cells for analyses and doesn't rely on capture of proteins expressed on cells", AACC, Jul. 26, 2011, A-27.

*Primary Examiner* — Jill Warden
*Assistant Examiner* — Brittany Fisher
(74) *Attorney, Agent, or Firm* — Olympic Patent Works PLLC

(57) ABSTRACT

Tube and float systems for analyzing target materials of a suspension include in which at least a portion of the outer surface of the float is reflective are described. The target material particles can be conjugated with fluorophores. In order to identify the target material, the material between the float and tube is illuminated with one or more channels of excitation radiation, which causes the fluorophores to become excited and emit radiation at longer wavelengths. The reflective surface of the float reflects the excitation radiation and the emitted radiation.

24 Claims, 7 Drawing Sheets

(56) References Cited

U.S. PATENT DOCUMENTS

| | | |
|---|---|---|
| 7,629,176 B2 | 12/2009 | Haubert et al. |
| 7,915,029 B2 | 3/2011 | Haubert et al. |
| 7,919,049 B2 | 4/2011 | Haubert et al. |
| 7,927,789 B1 * | 4/2011 | Baird et al. ......... 435/4 |
| 7,977,053 B2 * | 7/2011 | Thomas ......... 435/6.12 |
| 8,012,742 B2 | 9/2011 | Haubert et al. |
| 2005/0118589 A1 * | 6/2005 | Vann et al. ......... 435/6 |
| 2007/0284550 A1 * | 12/2007 | Smith et al. ......... 250/573 |
| 2008/0131868 A1 * | 6/2008 | Haubert et al. ......... 435/2 |
| 2010/0074803 A1 | 3/2010 | Haubert et al. |
| 2010/0317106 A1 | 12/2010 | Levine et al. |

\* cited by examiner

TUBE AND REFLECTIVE FLOAT SYSTEMS FOR ANALYZING SUSPENSIONS

CROSS-REFERENCE TO A RELATED APPLICATION

This application claims the benefit of Provisional Application No. 61/577,866, filed Dec. 20, 2011.

TECHNICAL FIELD

This disclosure relates generally to density-based fluid separation and, in particular, to tube and float systems for the separation and axial expansion of constituent suspension components layered by centrifugation.

BACKGROUND

Suspensions often include materials of interest that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as ova, fetal cells, endothelial cells, parasites, bacteria, and inflammatory cells, and viruses, including HIV, cytomegalovirus, hepatitis C virus, and Epstein-Barr virus. Currently, practitioners, researchers, and those working with blood samples try to separate, isolate, and extract certain components of a peripheral blood sample for examination. Typical techniques used to analyze a blood sample include the steps of smearing a film of blood on a slide and labeling the film in a way that enables certain components to be examined by bright field microscopy.

On the other hand, materials of interest composed of particles that occur in very low numbers are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers, but CTCs occur in very low numbers in peripheral whole blood samples. For instance, a 7.5 ml sample of peripheral whole blood that contains as few as 5 CTCs is considered clinically relevant in the diagnosis and treatment of a cancer patient. However, detecting even 1 CTC in a 7.5 ml blood sample is equivalent to detecting 1 CTC in a background of about 40 billion red and white blood cells. Using existing techniques to find, isolate and extract as few as 5 CTCs of a whole blood sample is extremely time consuming, costly and may be impossible to accomplish. As a result, practitioners, researchers, and those working with suspensions continue to seek systems and methods to more efficiently and accurately detect, isolate and extract target materials of a suspension.

SUMMARY

Systems for analyzing target materials of a suspension include a tube and a float in which at least a portion of the outer surface of the float is reflective. The target material particles are conjugated with fluorophores, and the tube, float and suspension are centrifuged so that at least a portion of the target material is located between the inner wall of the tube and the reflective surface of the float. In order to identify the target material, the material between the float and tube is illuminated with one or more channels of excitation radiation, which causes the fluorophores to become excited and emit radiation at longer wavelengths. The reflective surface of the float reflects the excitation radiation and the emitted radiation. As a result, the reflected excitation radiation may excite fluorophores that are not able to be directly illuminated by the excitation radiation and the reflected emitted radiation increases the total intensity of the emitted radiation.

DETAILED DESCRIPTION

The detailed description is organized into four subsections: A general description of tube and float systems is provided in a first subsection. Examples of reflective floats are provided in a second subsection. Using tube and reflective float systems to analyze target materials of a suspension is provided in a third subsection. And experimental results that contrast performance of a white float with a black float are presented in a fourth subsection.

In the following description, the term "light" is used to describe various uses and aspects of tube and reflective float systems. The term light is not intended to be limited to describing electromagnetic radiation in the visible portion of the electromagnetic spectrum, but is also intended to describe radiation in the ultraviolet and infrared portions of the electromagnetic spectrum.

General Description of Tube and Float Systems

Figure 1A:
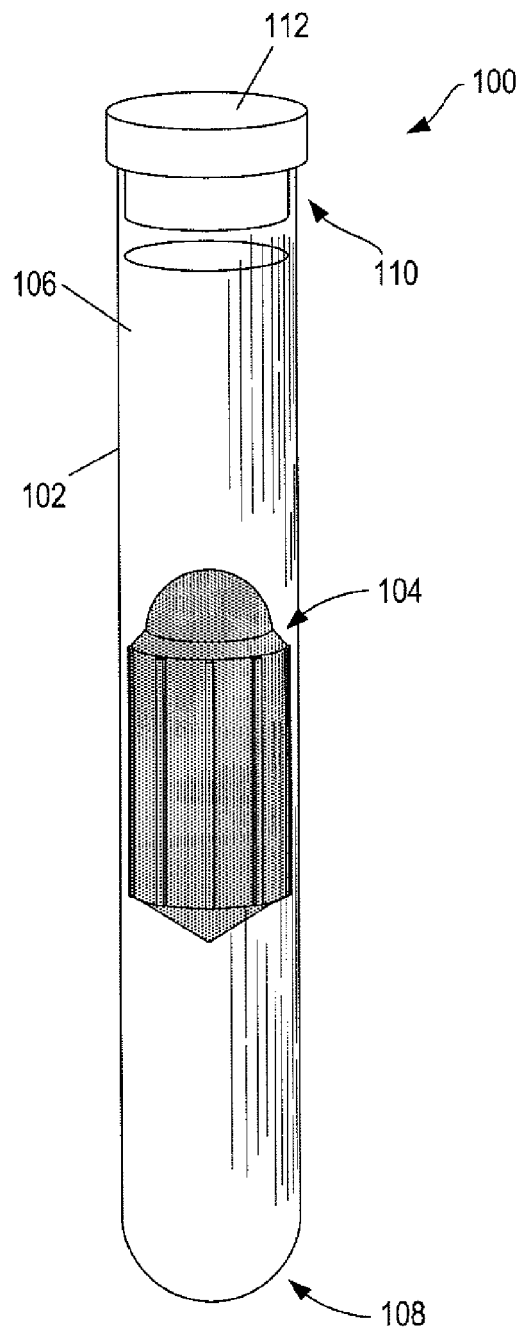
FIGS. 1A-1B show isometric views of two example tube and float systems.
Figure 1B:
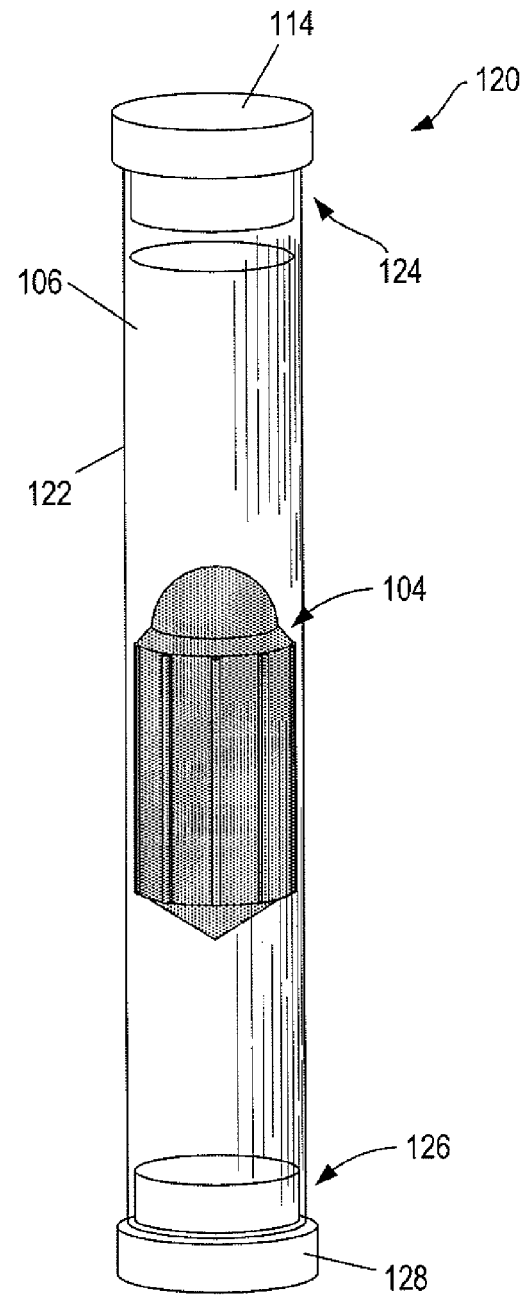

FIG. 1A shows an isometric view of an example tube and float system 100. The system 100 includes a tube 102 and a float 104 suspended within a suspension 106. In the example of FIG. 1A, the tube 102 has a circular cross-section, a first closed end 108, and a second open end 110. The open end 110 is sized to receive a stopper or cap 112. A tube may also have two open ends that are sized to receive stoppers or caps, such as the tube 122 of an example tube and float system 120 shown FIG. 1B. The system 120 is similar to the system 100 except the tube 102 of the system 100 is replaced by a tube 122 that includes two open ends 124 and 126 configured to receive the cap 112 and a cap 128, respectively. The tubes 102 and 122 have a generally cylindrical geometry, but may also have a tapered geometry that widens toward the open ends 110 and 124, respectively. Although the tubes 102 and 122 have a circular cross-section, in other embodiments, the tubes 102 and 122 can have elliptical, square, triangular, rectangular, octagonal, or any other suitable cross-sectional shape that substantially extends the length of the tube. The tubes 102 and 122 can be composed of a transparent or semitransparent flexible material, such as flexible plastic or another suitable material.

Figure 2A:
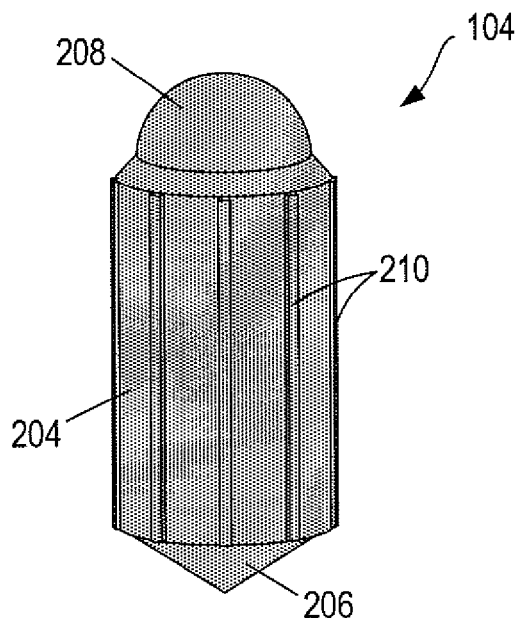
FIGS. 2A-2D shows four examples of floats with different types of structural elements and end caps.
Figure 2B:
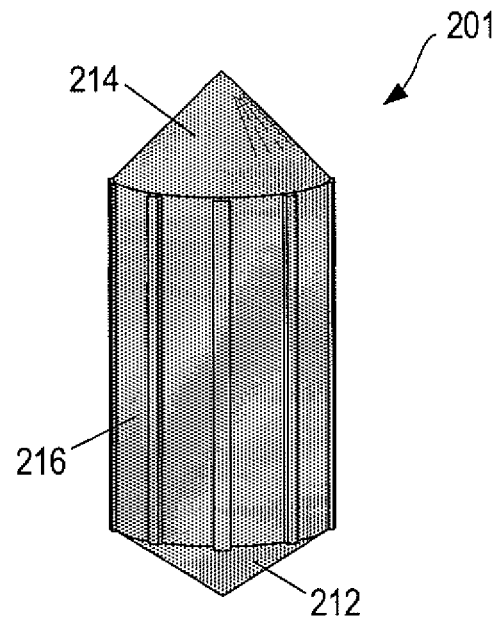
Figure 2C:
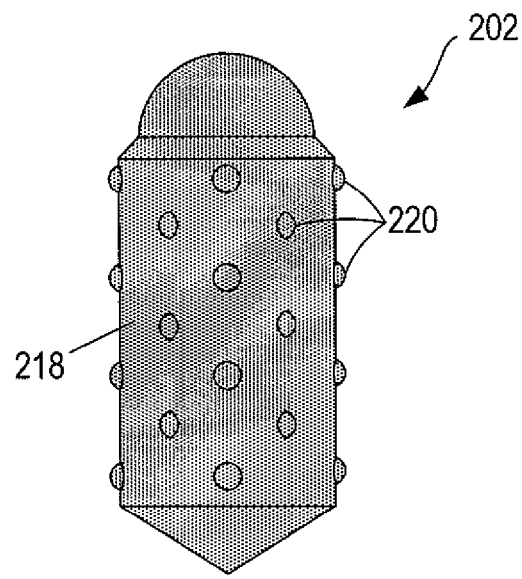
Figure 2D:
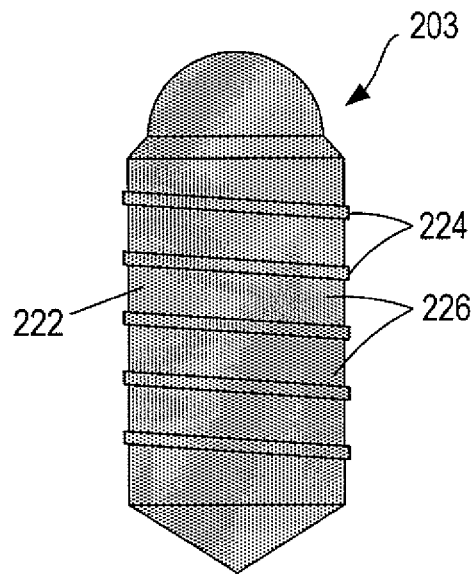

FIGS. 2A-2D shows four examples of floats 104 and 201-203 with different types of structural elements and end caps. In FIG. 2A, the float 104, shown in FIG. 1, includes a main body 204, a cone-shaped end cap 206, a dome-shaped end cap 208, and structural elements in the form of splines 210 that are radially spaced and axially oriented. The splines 210 provide a sealing engagement with the inner wall of the tube 102. In other embodiments, the number of splines, spline spacing, and spline thickness can be independently varied. The splines 210 can also be broken or segmented. The main body 204 is sized to have an outer diameter that is less than the inner diameter of the tube 102, thereby defining fluid retention channels between the outer surface of the body 204 and the inner wall of the tube 102. The outer surfaces of the body 204 between the splines 210 can be flat, curved or have another suitable geometry. In the example of FIG. 2A, the splines 210 and the body 204 form a single structure. Embodiments include other types of geometric shapes for float end caps. In FIG. 2B, an example float 201 has two cone-shaped end caps 212 and 214. The main body 216 of the float 201 includes the same structural elements (i.e., splines) as the float 104. A float can also include two dome-shaped end caps. Float end caps can be configured with other geometric shapes and are not intended to be limited to the shapes described herein. In other embodiments, the main body of a float can include a variety of different structural elements for separating target materials, supporting the tube wall, or directing the suspension fluid around the float during centrifugation. FIGS. 2C and 2D show examples of two different types of main body structural elements. Embodiments are not intended to be limited to these two examples. In FIG. 2C, the main body 218 of the float 202 is similar to the float 104 except the main body 218 includes a number of protrusions 220 that provide support for the deformable tube. In other embodiments, the number and pattern of protrusions can be varied. In FIG. 2D, the main body 222 of the float 203 includes a single continuous helical structure or ridge 224 that spirals around the main body 222 creating a helical channel 226. In other embodiments, the helical ridge 224 can be rounded or broken or segmented to allow fluid to flow between adjacent turns of the helical ridge 224. In other embodiments, the helical ridge spacing and rib thickness can be independently varied.

The floats can be composed of a rigid organic or inorganic materials, and rigid plastic materials, such as polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides ("PPO"), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrile butadiene-styrene copolymer and others.

Examples of Reflective Floats

Figure 3A:
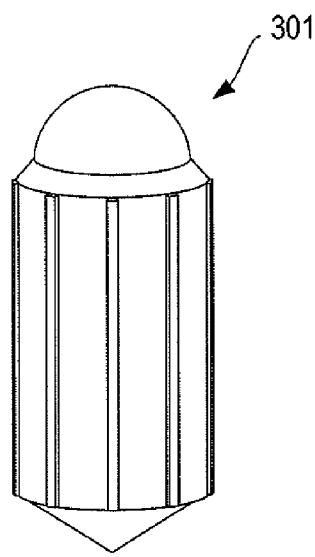
FIGS. 3A-3C show three example reflective floats.
Figure 3B:
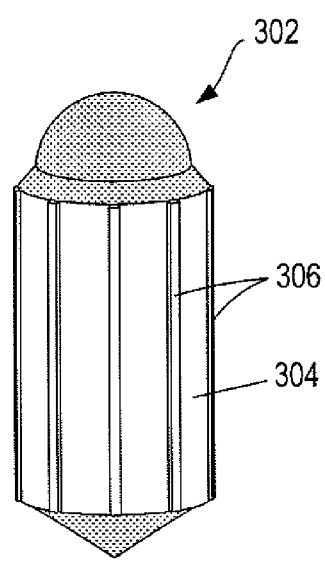
Figure 3C:
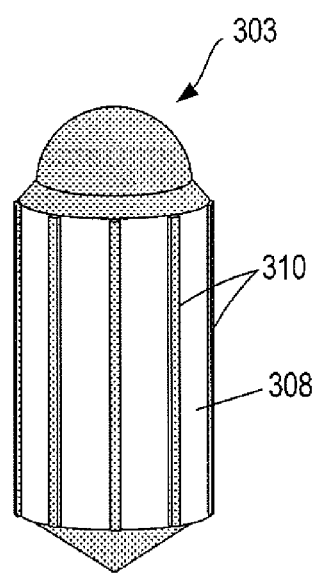

The floats described above with reference to FIGS. 1 and 2 are shaded to represent dark colored floats. When a dark colored float is used to trap a target material between the outer surface of the float and the inner wall of a tube and the target material is imaged by illuminating the material the float and the tube. But a dark colored float may absorb an appreciable amount of the light, which may cause the float to heat up and expand within the tube, which, in turn, may cause target material particles to change position. This shift in particle position makes it difficult and time consuming to relocate target particles because the particles have randomly moved to different locations. In order to reduce the amount by which target particles shift when the target material is illuminated, a reflective float with a reflective outer surface can be used. FIGS. 3A-3C show three different example reflective floats 301-303. The reflective floats 301-303 are similar to the float 104 except the floats 301-303 include one or more reflective surfaces represented by unshaded regions. In FIG. 3A, the entire outer surface of the float 301 is reflective. In FIG. 313, the outer surface of main body portion 304, including the structural elements or splines 306, is a reflective surface. In FIG. 3C, outer surfaces of main body portion 308, excluding structural elements or splines 310, are reflective surfaces.

A reflective float can be created by adding a highly reflective or white pigment to the material composition of the float. A reflective float can be created by combining the rigid organic and inorganic materials listed above with a white pigment during fabrication of the float. As a result, the entire float is reflective, as shown in the example of FIG. 3A. The float can have a glossy or matte finish. Examples of white plastics that can be used for a reflective float include, but are not limited to, white Delrin®, moisture resistance polyester, wear-resistant slippery cast nylon 6, impact-resistant slippery UHMW polyethylene, opaque white polypropylene, rigid HDPE polyethylene, UV resistant VHMW polyethylene, acrylic PVC, flame-retardant polypropylene, moisture-resistant LDPE polyethylene, lightweight rigid PVC foam, structural fiberglass, and white polystyrene. A reflective surface of a float can be a reflective coating applied to the outer surface of the float. For example, the coating can be a reflective paint, such as white paint, paint with reflective particles or ceramic beads or a reflective polymer. The paint can have a glossy or matte finish. A reflective surface of a float can be a reflective plating applied to the outer surface of the float. For example, the plating can be a shiny reflective metal, ceramic, or a mirror. Suitable reflective metals include, but are not limited to, gold, silver, aluminum, tin, copper, bronze, chromium, cobalt, nickel, palladium, platinum, manganese, zinc, titanium, niobium, molybdenum, tungsten, or a suitable metalloid. The reflective outer surface can also be created by reflective objects or particles attached to the outer surfaces of the float using an adhesive or embedded in the outer surface of the float.

Figure 4A:
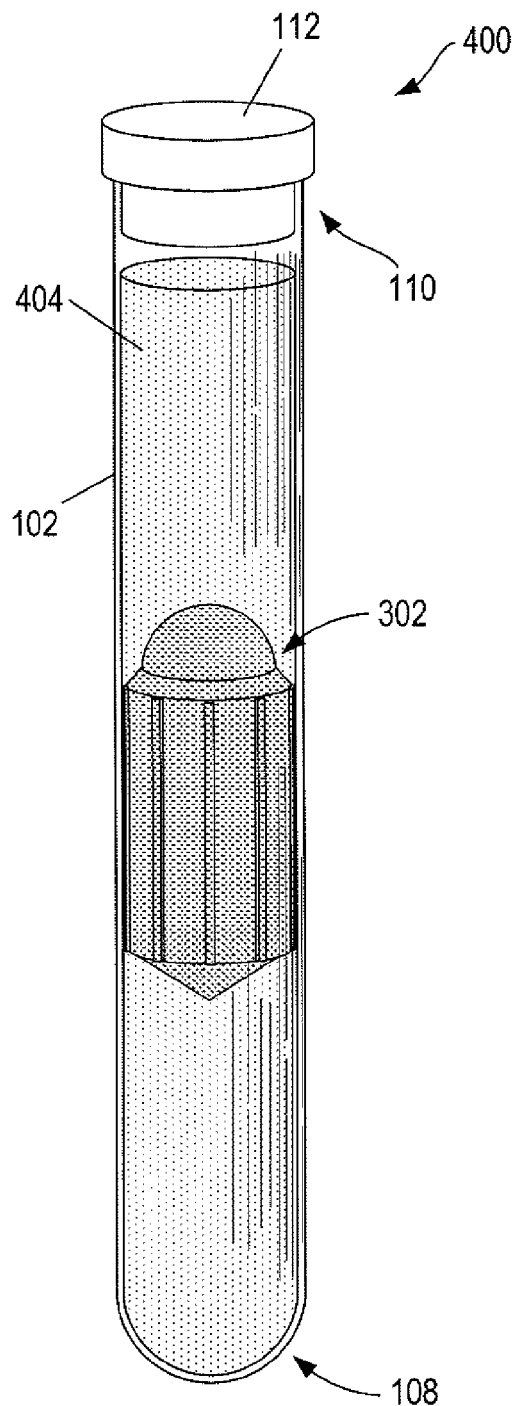
FIGS. 4A-4B show an example tube and reflective float system used with a suspension containing a target material.
Figure 4B:
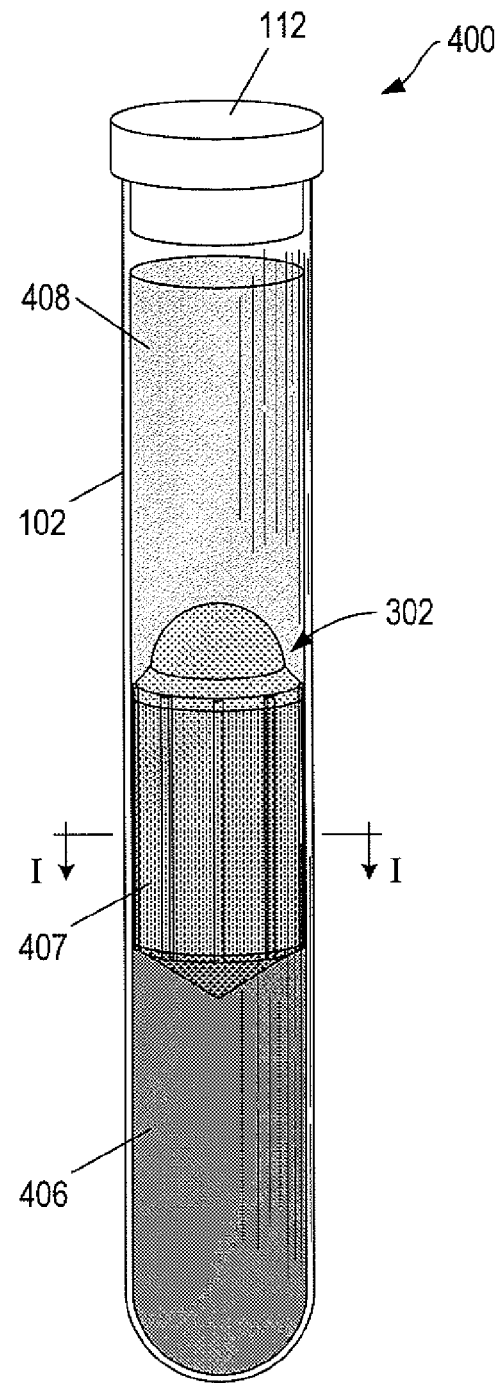

Using Tube and Reflective Float Systems to Analyze Target Materials of a Suspension FIGS. 4A-4B show an example tube and reflective float system 400 used with a suspension containing a target material. The system 400 is similar to the system 100 describe above with reference to FIG. 1 except the float 104 has been replaced by the reflective float 302. In the example of FIG. 4A, the reflective float 302 is deposited in the tube 102 along with a suspension 404 that contains a target material. The float 302 has a density that approximately matches the density of the target material. Prior to introducing the float 302 to the tube 102, the suspension is mixed with a solution that contains fluorescent probes. The fluorescent probes can be fluorescent chemical compounds called "fluorophores" attached to ligands that selectively bind to the target material particles. In other words, the target material particles are fluorescently labeled. When the tube 102, float 302 and suspension 404 are centrifuged together for a period of time, the suspension materials separate into layers along the axial length of the tube according the density associated with each layer with higher density materials settling beneath lower density materials. In the example of FIG. 4B, centrifugation is used to separate the suspension 404 into three layers 406-408. Any unattached fluorescent probes are present in the top layer 408 above the float 302. Because the float 302 has a density that approximately matches the density of the target material, the float 302 is positioned at approximately the same level as the layer 407 and expands the axial length of the layer 407 between the main body of the float 302 and the inner wall of the tube 102. The layer 407 contains the target material with fluorescently labeled target material particles located within the channels between the main body of the float 302 and the inner wall of the tube 102.

The suspension 404 can be a biological suspension, such as whole blood, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. The target material particles can be cells, such as ova or circulating tumor cells, parasites, microorganisms, or inflammatory cells. The target particles may have a number of different types of receptor molecules located on the surface. Each type of receptor is a molecule capable of attaching a particular ligand. Examples of ligands include peptides, neurotransmitters, hormones, pharmaceutical drugs, toxins, and other types of molecules. As a result, ligands can be used to classify the target particles and determine the specific type of target particles present in the suspension by conjugating ligands that attach to particular receptors with a particular fluorophore. For example, each type of fluorophore emits light in a narrow wavelength range of the electromagnetic spectrum called a "channel" when an appropriate stimulus, such as light with a shorter wavelength, is applied. A first type of fluorophore that emits light in the green channel can be attached to a first ligand that binds specifically to a first type of receptor, while a second type of fluorophore that emits light in the red channel can be attached to a second ligand that binds specifically to a second type of receptor. The channel color observed as a result of stimulating the target material identifies the type of receptor, and because receptors can be unique to particular target particles, the channel color can also be used to identify the target particle. Examples of suitable fluorophores include, but are not limited to, fluorescein, FITC ("fluorescein isothiocyanate"), phycoerythrin, Cy5PE, Cy7PE, Texas Red, allophycocyanin, Cy5, Cy7APC, cascade blue, biotin, DAPI ("4', 6-diamidino-2-phenylindole") and TRITC ("tetramethylrhodamine isothiocyanate").

In practice, a suspension including a target material is added to a tube along with a reflective float and the tube, float and suspension are centrifuged to trap target material particles between the float and the tube, as described above. The target particles can be fixed, permeabilized, and labeled. The target material is imaged by illuminating the tube with different wavelengths of excitation light that excite the different fluorophores. The light emitted from the excited fluorophores is captured in images by a scanner camera, allowing the target particles to be enumerated identified based on the channel of the light emitted.

Figure 5:
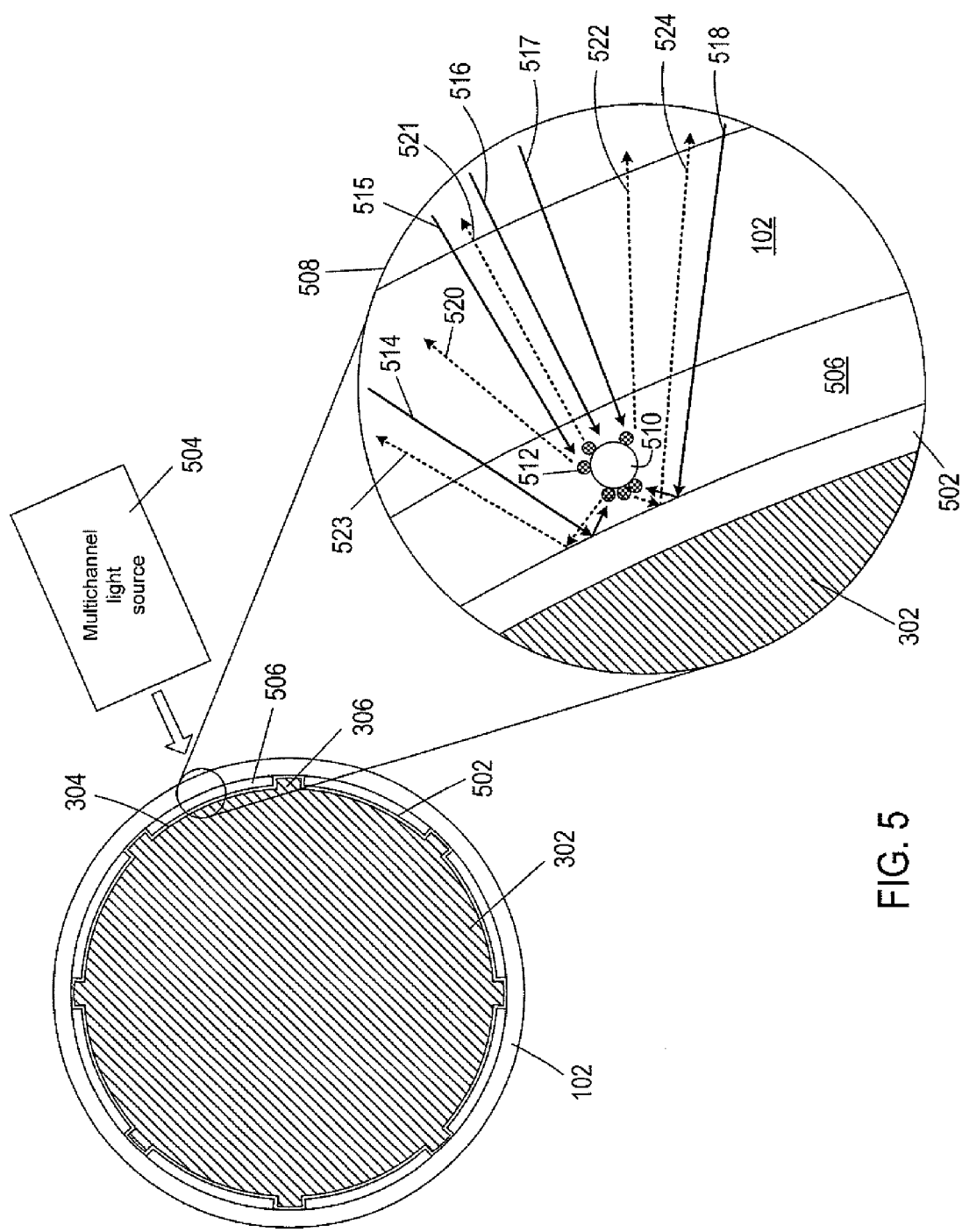
FIG. 5 shows a cross-sectional view of the tube and reflective float system along a line I-I shown in FIG. 4B.

The reflective surface of a reflective float can increase the intensity of light emitted from the fluorophores. FIG. 5 shows a cross-sectional view of the system 400 along a line I-I shown in FIG. 4B. In the example of FIG. 5, the cross-sectional view reveals that the main body 304 of the reflective float 302 is coated with a reflective layer 502. A multichannel light source 504 illuminates the target material in a channel 506 with excitation light to excite fluorophores attached to target material particles. FIG. 5 includes a magnified view 508 of a portion of the channel 506. Circle 510 represents a target material particle and smaller shaded circles, such as circle 512, represent six fluorophores attached to the particle 510 via ligands. Solid-line directional arrows 514-518 represent rays of excitation light associated with a channel output from the source 504. As shown in FIG. 5, rays 515-517 pass through the tube 102 to illuminate the fluorophores facing the tube 102. Dashed-line directional arrows 520-522 represent rays of light emitted from the fluorophores that face the tube 102. Rays 514 and 518 represent excitation light that is reflected off of the reflective layer 502 to illuminate fluorophores that face the float 302. Dashed-line directional arrows 523 and 524 represent rays of excitation light emitted from the fluorophores that face the float 302.

Note that without the reflective layer 502, much of the light represented by the rays 514 and 518 is absorbed by the float 302 and is not available to excite the fluorophores that face the float 302. In the example of FIG. 5, the light emitted from the fluorophores that face the float 302 is also reflected from the reflective layer 502 and adds to the intensity of the light emitted from the fluorophores that face the tube 102. As a result, images of the particle 510 appear brighter than the particle 510 would otherwise appear with a dark colored or non-reflective float. Note also that because the excitation light and the emitted light are not absorbed by the float 302, the float 302 does not heat up and expand. As a result, the particle 510 is less likely to shift, making it easier to identify the location of the particle 510 and the same particle 510 can be relocated when the target material is illuminated a second time.

The reflective surface of a reflective float can also be functionalized to attract or attach target particles to the float. The reflective surface may be functionalized using a self-assembled monolayer comprising a head, a tail, and a functional group. The head reacts with and attaches to the reflective surface, and may be any chemical having a high affinity for the reflective surface. For example, sulfur has a high affinity for metals. The tail can be a carbon backbone that connects the head to the functional group and may be any suitable length and may or may not be branched. The functional group is selected based on the appropriate functionality or reaction desired. Examples of self-assembled monolayers include alkanethiols for metals and silanes for nonmetallic oxides. After the reflective surface has been functionalized, materials may be added the suspension to provide better capture of the target particles. The materials include Mytilus edulis foot protein ("Mefp"); biopolymers; polyphenolic proteins (including those polyphenolic proteins containing L-DOPA); chemo-attractant molecules, such as epidermal growth factor ("EGF") or vascular endothelial growth factor ("VEGF"); an extracellular matrix protein ("ECM"); maleic anhydride; maleimide activated sulfa-hydryl groups, poly-L-lysine; poly-D-lysine; streptavidin; neutravidin; protein A; protein G; protein A/G, protein L; biotin; glutathione; antibodies; recombinant antibodies; aptamers; RGD-peptides; fibronectin; collagen; elastin; fibrillin; laminin; or proteoglycans.

Experimental Results

Figure 6A:
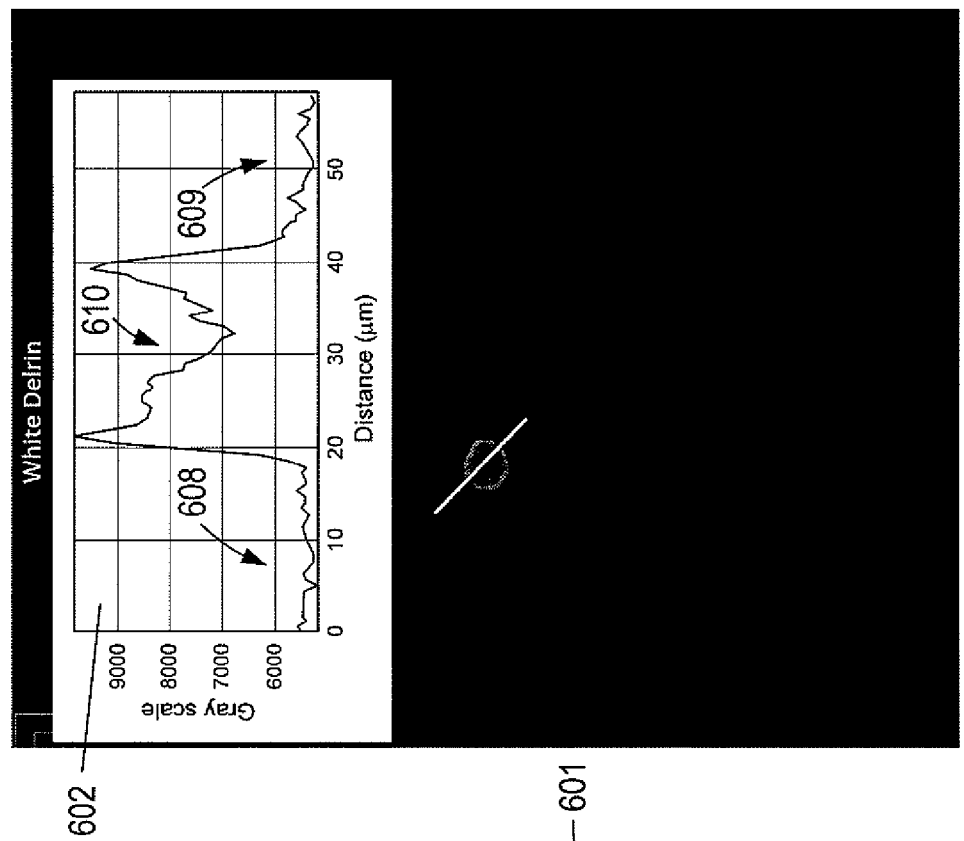
FIG. 6A shows a black and white image of a first fluorescently labeled cell using a tube and non-reflective float system.
Figure 6B:
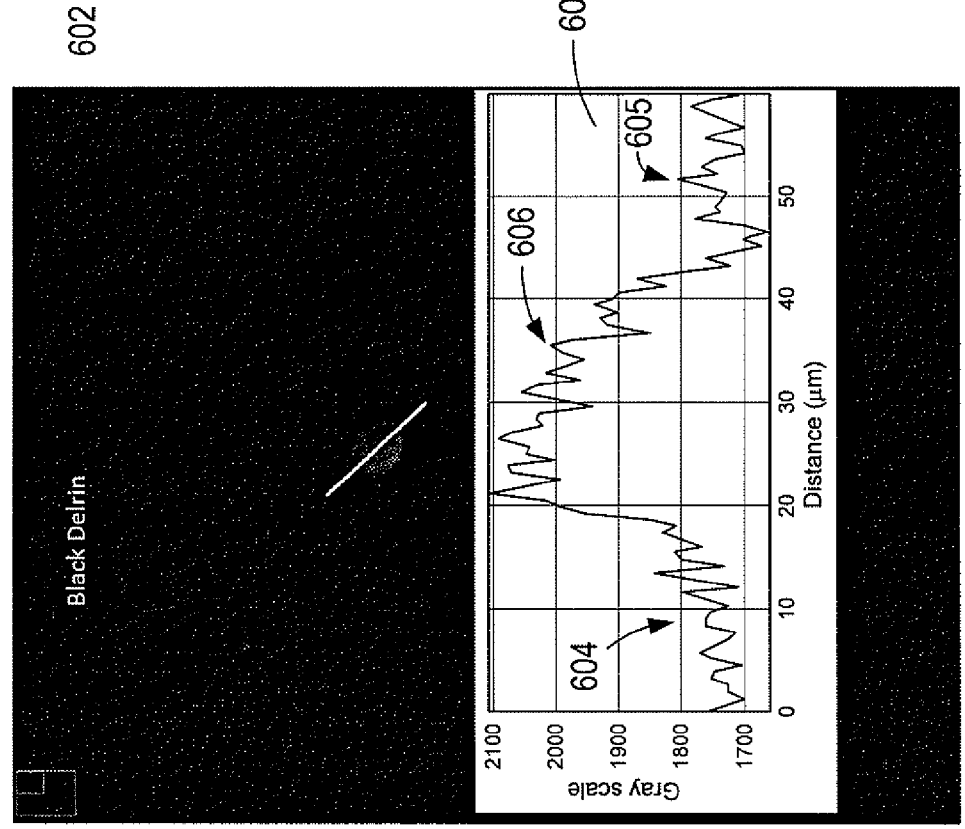
FIG. 6B shows a black and white image of a second fluorescently labeled cell using a tube and reflective float system.

Experimental results obtained from comparing a reflective float composed of white Deirin® float and a black float composed of black Deirin® are now described. The floats were placed in separate tubes, each with a whole blood sample containing circulating tumor cells ("CTCs"). The tube and float systems were centrifuged and imaged as described above. FIG. 6A shows a black and white image of a first CTC labeled with TRITC using a tube and float system in which the float is composed of black Deirin®. FIG. 6B shows a black and white image of a second CTC also labeled with TRITC but the float of the tube and float system is composed of white Delrin®. FIGS. 6A and 6B both include gray scale intensity versus distance plots 601 and 602. The plot 601 represents the recorded intensity versus distance for the first cell along a white line, shown in FIG. 6A, that bisect the first cell. The plot 602 represents the recorded intensity versus distance for the second cell along a white line, shown in FIG. 6B, that bisect the second cell. The image of the first CTC and the intensity plot 601 where obtained for an exposure time of approximately 0.05 seconds, and the image of the second CTC and intensity plot 602 where obtained for an exposure time of approximately 0.2 seconds. In FIG. 6A, regions 604 and 605 of the plot 601 correspond to background light and hump 606 represents the intensity across the first CTC along the corresponding white line. The jagged appearance of the intensity in plot 601 represents the graininess of the image shown in FIG. 6A. Plot 601 reveals that the intensity of the first CTC above the background ranges from about 50 to about 450, with the greatest intensity appearing near the middle of the first CTC. In FIG. 6B, regions 608 and 609 of the plot 602 correspond to background light, while hump 610 represents the intensity across the second CTC along the corresponding white line. Plot 602 reveals that the intensity of the second CTC above the background ranges from about 1000 to about 4500, with the greatest intensities occurring around the perimeter CTC image. In the image of FIG. 6B, the second CTC has a brighter perimeter than the first CTC shown in FIG. 6A because more TRITC labels located around the perimeter of the second CTC are excited by the excitation light reflected off of the white float. In other words, the signal-to-noise ratio is greater for the white float than for the black float.

Figure 7:
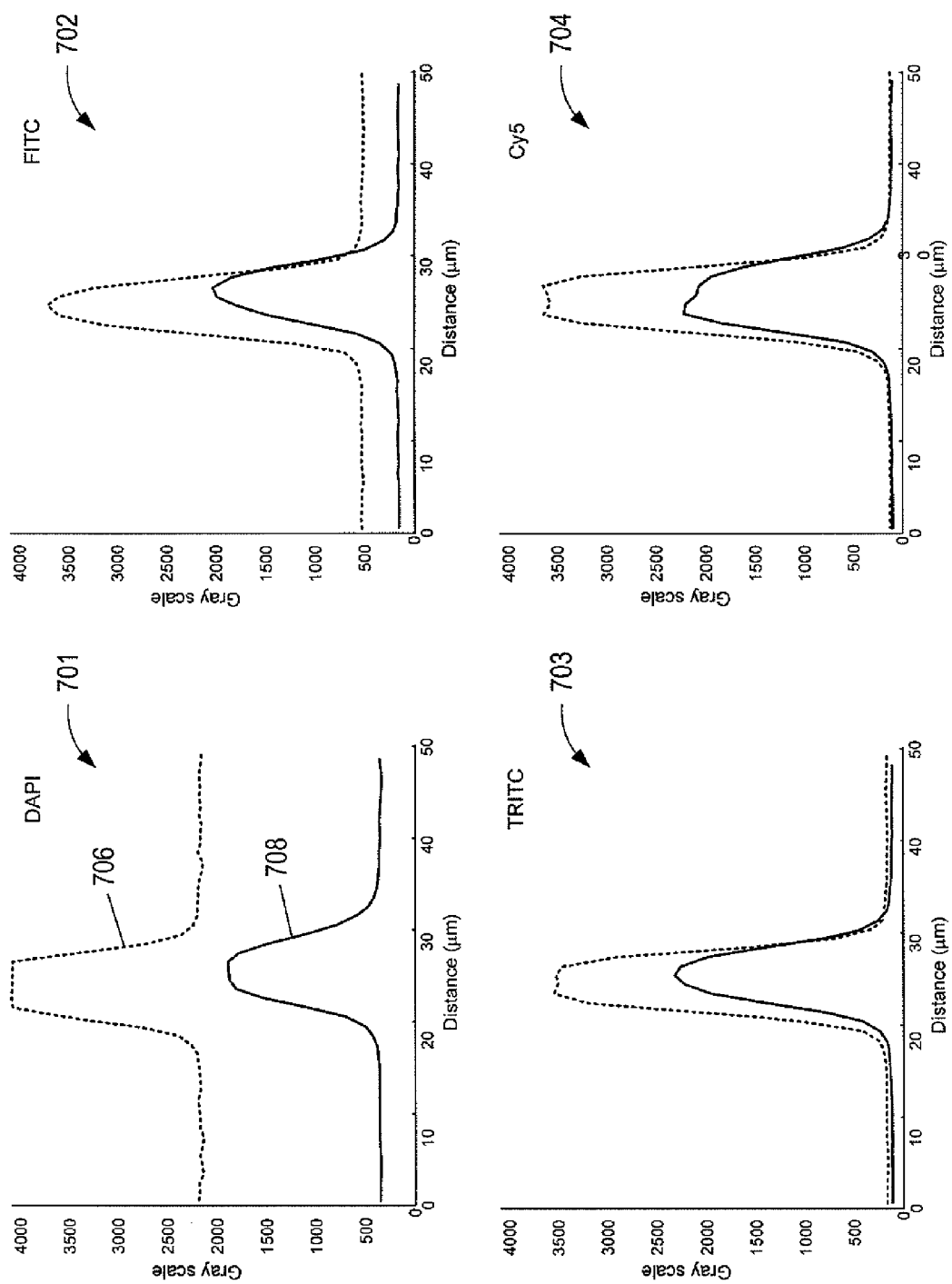
FIG. 7 shows four gray scale intensity versus distance plots, each plot associated with a cell labeled with a different fluorophore.

FIG. 7 shows four different gray scale intensity plots 701-704 associated with four cells, each plot corresponds to a different fluorophore. Plots 701-704 were obtained for CTCs of a whole blood sample labeled with DAPI, FITC, TRITC, and Cy5, respectively. Dashed-line curves, such as curve 706, represent the gray scale intensity across the cells obtained from tube and float systems in which the floats were composed of white Delrin®. Solid-line curves, such as curve 708, represent the gray scale intensity across cells obtained from tube and float systems in which the floats were composed of black Delrin®. The peaks, such as peak 710, represent the intensity of the light emitted from the fluorescent labels of the cells and flat regions surrounding the peaks represent the intensity of the background light. Plots 701-704 all reveal that the intensity difference between the cells and the associated backgrounds were greater for the white float than for the black float. In other words, for the four types of fluorophores analyzed, the white float produces a larger signal-to-noise ratio than the black float.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

The invention claimed is:

1. A system for analyzing a target material of a suspension, the system comprising:
   a tube with a closed end to hold the suspension; and
   a reflective float to be added to the tube, wherein the float is to trap the target material between the float and an inner wall of the tube and at least a portion of an outer surface of the float is reflective with respect to excitation light to illuminate fluorophores to be attached to particles of the target material and to light emitted from the fluorophores.

2. The system of claim 1, wherein the at least a portion of the outer surface of the float is reflective further comprises an entire outer surface of the float is reflective.

3. The system of claim 1, wherein the at least a portion of the outer surface of the float is reflective further comprises a main body portion of the float is reflective.

4. The system of claim 1, wherein the at least a portion of the outer surface of the float is reflective further comprises a main body portion of the float is reflective except for the structural elements that protrude from the main body portion of the float.

5. The system of claim 1, wherein the reflective float is composed of a reflective material.

6. The system of claim 5, wherein the reflective material further comprises one of a metal, a ceramic, or a white pigmented polymer.

7. The system of claim 1, wherein the at least a portion of the outer surface of the float is reflective farther comprises a reflective coating applied to the outer surface.

8. The system of claim 1, wherein the at least a portion of the outer surface of the float is reflective further comprises a reflective plating attached to the outer surface.

9. The system of claim 1, wherein the at least a portion of the outer surface of the float is reflective further comprises reflective particles attached to the outer surface.

10. The system of claim 1, wherein the at least a portion of the outer surface of the float is reflective further comprises reflective particles embedded within the outer surface.

11. The system of claim 1, wherein the reflective portion of the outer surface is functionalized to attract or attach particles of the target material to the float.

12. The system of claim 11, wherein a self-assembled monolayer comprising a head, a tail, and a functional group is used to functionalize the reflective surface.

13. A float to be inserted into a tube with a closed end to hold a suspension, wherein the float is to trap a target material of a suspension between the float and an inner wall of the tube and the float includes a reflective outer surface to reflect excitation light used to illuminate fluorophores attached to target particles of the target material and to reflect light emitted from the fluorophores.

14. The float of claim 13, wherein the reflective outer surface is an entire outer surface of the float.

15. The float of claim 13, wherein the reflective outer surface is a main body portion of the float.

16. The float of claim 13, wherein the reflective outer surface is a main body portion of the float except for structural elements that protrude from the main body portion of the float.

17. The float of claim 13, wherein the float is composed of a reflective material.

18. The float of claim 17, wherein the reflective material further comprises one of a metal, a ceramic, or a white pigmented polymer.

19. The float of claim 13, wherein the reflective outer surface is a reflective coating applied to the outer surface of the float.

20. The float of claim 13, wherein the reflective outer surface is a reflective plating attached to the outer surface of the float.

21. The float of claim 13, wherein the reflective outer surface further comprises reflective particles attached to the outer surface of the float.

22. The float of claim 13, wherein the reflective outer surface further comprises reflective particles embedded within the outer surface of the float.

23. The float of claim 13, wherein the reflective outer surface is functionalized to attract or attach particles of the target material to the float.

24. The float of claim 23, wherein a self-assembled monolayer comprising a head, a tail, and a functional group is used to functionalize the reflective outer surface.

* * * * *